US011484816B2

(12) United States Patent
Deregibus et al.

(10) Patent No.: US 11,484,816 B2
(45) Date of Patent: Nov. 1, 2022

(54) ISOLATION OF EXTRACELLULAR VESICLES (EVS) FROM BIOLOGICAL FLUID SAMPLES

(71) Applicant: UNICYTE EV AG, Oberdorf (CH)

(72) Inventors: Maria Chiara Deregibus, Turin (IT); Federico Figliolini, Volpiano (IT); Ciro Tetta, Mirandola (IT); Giovanni Camussi, Turin (IT)

(73) Assignee: UNICYTE EV AG, Oberdorf (CH)

( * ) Notice: Subject to any disclaimer, the term of this patent is extended or adjusted under 35 U.S.C. 154(b) by 1021 days.

(21) Appl. No.: 16/093,471

(22) PCT Filed: Apr. 11, 2017

(86) PCT No.: PCT/EP2017/058649
§ 371 (c)(1),
(2) Date: Oct. 12, 2018

(87) PCT Pub. No.: WO2017/178472
PCT Pub. Date: Oct. 19, 2017

(65) Prior Publication Data
US 2020/0179827 A1  Jun. 11, 2020

(30) Foreign Application Priority Data

Apr. 12, 2016 (EP) .................................. 16164889

(51) Int. Cl.
*B01D 21/01* (2006.01)
*B01D 21/26* (2006.01)
(52) U.S. Cl.
CPC ........... *B01D 21/01* (2013.01); *B01D 21/262* (2013.01)
(58) Field of Classification Search
CPC ..... B01D 21/01; B01D 21/262; C12Q 1/6806
See application file for complete search history.

(56) References Cited

U.S. PATENT DOCUMENTS 6,680,046 B1 * 1/2004 Boschetti ........... A61K 47/6927
424/9.1
8,901,284 B2    12/2014 Vlassov et al.
(Continued)

FOREIGN PATENT DOCUMENTS

CN        103100093        5/2013
JP        2007271388 A  * 10/2007
(Continued)

OTHER PUBLICATIONS

Yassin et al., Protamine-adsorbed magnetic nanoparticles for efficient isolation and concentration of hepatitis-C virus from human plasma samples. Chem Communications, vol. 50, No. 5, Jan. 1, 2014, pp. 590-592.
(Continued)

*Primary Examiner* — James C Goloboy
(74) *Attorney, Agent, or Firm* — Jacobson Holman PLLC

(57) ABSTRACT

The invention relates to compositions and methods for isolating extracellular vesicles (EVs) from a biological fluid sample. The compositions and methods of the invention are based on the combination of a polycation with an extracellular matrix forming polymer. Extracellular vesicles (EVs) are isolated from biological fluids such as blood, serum, plasma, saliva, urine or cerebrospinal fluid, or from the conditioned medium of a cell culture, such as an adult stem cell culture. The use of the isolation methods and compositions of the invention results in a higher EVs recovery, enrichment in exosomes, simplicity, cost-effectiveness, and in the isolation of EVs that retain their biological activities in vitro.

15 Claims, 5 Drawing Sheets

(56) References Cited

U.S. PATENT DOCUMENTS

| | | | |
|---|---|---|---|
| 9,005,888 B2 | 4/2015 | Antes et al. | |
| 2013/0337440 A1* | 12/2013 | Antes | C12Q 1/6895 435/6.1 |

FOREIGN PATENT DOCUMENTS

| | | |
|---|---|---|
| WO | WO 2013/158203 | 10/2013 |
| WO | WO 2013/188832 | 12/2013 |
| WO | WO 2015/131153 | 9/2015 |

OTHER PUBLICATIONS

Taylor et al. Exosome Isolation for Proteomic Analyses and RNA Profiling. Clinical Applications of Mass Spectrometry, vol. 728, Jan. 1, 2011, pp. 235-246.

Szatanek et al. Isolation of extracellular vesicle: Determining the correct approach (Review), International Journal of Molecular Medicine, 36: 11-17, 2015.

Herrera et al. Isolation and Characterization of a Stem Cell Population from Adult Human Liver, Stem Cells, 2006; 24: 2840-2850.

Ratajczak et al. Membrane-derived microvesicles: important and underappreciated mediators of cell-to-cell communication. Leukemia (2006) 20, 1487-1495.

Herrera et al. Human liver stem cell-derived microvesicles accelerate hapatic regeneration in hepatectomized rats. J. Cell. Mol. Med. vol. 14, No. 6B, 2010, pp. 1605-1618.

Cantaluppi et al. Macrophage stimulating protein may promote tubular regneration after acute injury. J. Am Soc. Nephrol. 19: 1904-1918, 2008.

Iavello et al. Role of Alix in miRNA packaging during extracellular vesicle biogenesis. International Journal of Molecular Medicine. 37: 958-966, 2016.

Witwer et al. Standardization of sample collection, isolation and analysis methods in extracellular vesicle research, J. Extracell Vesicles 2: 20360, 2013.

Momen-Heravi et al. Impact of biofluid viscosity on size and sedimentation efficiency of the isolated microvesicles. Frontiers in Physiology, vol. 3, article 162, May 29, 2012.

\* cited by examiner

ISOLATION OF EXTRACELLULAR VESICLES (EVS) FROM BIOLOGICAL FLUID SAMPLES

The present invention relates to a method of isolating extracellular vesicles (EVs) from a biological fluid sample and to a composition for precipitation of extracellular vesicles (EVs) from a biological fluid sample.

Vesicular-mediated communication between cells appears critical in many biological processes. Small vesicles released from cells have recently emerged as important mediators of inter-cellular communication. These vesicles, that have been termed extracellular vesicles (EVs), are inclusive of exosomes released from the endosomal cell-membrane compartment and of microvesicles released from the cell surface by plasma membrane budding. The EV content of proteins, lipids and nucleic acids varies with the cell of origin and, after incorporation into recipient cells, they may transfer information which may change the phenotype and function of recipient cells.

Several studies have addressed the role of EVs in physiological and pathological conditions based on their biological activity and molecular constituents. Moreover, since EVs retain the signature of the cell of origin and are present in all body fluids, their potential use as diagnostics in different pathological conditions has been suggested.

A fundamental issue remains how to isolate EVs from cultured cells to study their biological functions or from biological fluids for diagnostic purposes. Since foetal bovine serum frequently used for cell culture is enriched in EVs, the in vitro experiments require the use of EVs-depleted serum. The isolation of EVs from body fluids, on the other hand, has to face the complexity due to the concomitant presence of EVs of different cellular origin. Therefore, in order to identify a potential biomarker, it is critical to discriminate cellular origin on the basis of EV molecular expression or content, by proteomic or genomic analysis. After removal of cell debris by centrifugation, three main methods are conventionally used for isolation of EVs, namely differential ultracentrifugation in the absence or presence of sucrose gradient, size exclusion chromatography and immune affinity. All these methods have some advantages, which are mainly related to the possibility to discriminate between different EV populations, and concerns, which are related to the risk of damaging vesicles during purification with loss of biological activity, to the need of a sufficiently large sample and to the efficiency of isolation.

Moreover, polymeric precipitation of EVs has been suggested as an alternative method mainly focused on the evaluation of RNA and protein content. The polymeric precipitation methods are based on the formation of a mesh-like net, which embeds EVs with a size ranging from 60 to 180 nm. Such methods may be applied either to culture media or to body fluids. In particular, polymeric precipitation methods may have the advantage for detection of biomarkers in vesicles derived from small biological samples.

Currently, the "gold standard" methods of EV purification are the differential ultracentrifugation or the density gradient ultracentrifugation. These methods, however, are influenced by several parameters difficult to standardize such as viscosity of solutions, rotor type, centrifugal radius and g force. In addition, the integrity of EVs after prolonged high speed ultracentrifugation may be damaged. In fact, membrane debris were observed by electron microscopy and difficulty in recovering RNA and exosomal proteins has been reported.

Several other approaches to EV purification have been investigated. The size exclusion chromatography may have an advantage on ultracentrifugation in maintaining EVs integrity, since with this method EVs are not subjected to shear stress. Filtration with membranes with appropriate pores is also an alternative, but it does not guarantee removal of several small contaminants and does not avoid loss of EVs by binding to membranes. Immunoaffinity purification may isolate specific exosome subtypes maintaining integrity of their cargo.

A limitation of most of these techniques is the efficiency in the recovery of sufficient amounts of EVs starting from small biological samples.

The polymeric precipitation technique, based on the ability of PEG to entrap EVs, has been shown to be a fast approach to EV isolation from biological samples. This technique has been developed on the observation that PEG allows virus precipitation and several products based on the use of PEG with 8000 Da molecular weight are commercially available.

U.S. Pat. No. 9,005,888 discloses a method of isolating cell secreted microvesicles from a liquid sample by the use of a precipitation solution comprising at least one species of polyethylene glycol (PEG) having a molecular weight of between 400 and 8,000 Daltons.

WO 2013/188832 discloses a method of isolating cell secreted microvesicles from a liquid sample by the use of a precipitation solution comprising at least one species of polyethylene glycol (PEG) having a molecular weight of about 8,000 Daltons or about 10,000 Daltons.

U.S. Pat. No. 8,901,284 discloses a method for the isolation of exosomes from a biological fluid sample by the use of a volume-excluding polymer such as polyethylene glycol, dextran, dextran sulfate, dextran acetate, polyvinyl alcohol, polyvinyl acetate, or polyvinyl sulfate.

In order to overcome the drawbacks of the prior art, in particular the complexity and expensiveness of the above-mentioned prior art methods, their low efficiency in EV recovery, the possible presence of contaminants in the isolated EVs and the risk of damaging EV membranes, the present invention provides a method of isolating EVs from biological fluid samples as defined below.

Further features and advantages of the method of the invention are defined in the dependent claims.

Also within the scope of the invention is a precipitation composition as defined below, which is suitable for use in the isolation method of the invention.

BRIEF DESCRIPTION OF THE DRAWINGS

FIGS. 5A and 5C graphically depict the results of in vitro scratch-wound healing assay testing using EVs isolated according to the present invention. FIGS. 5B-E are micrographs depicting the results of the in vitro scratch-wound healing assay testing.

Figure 1:
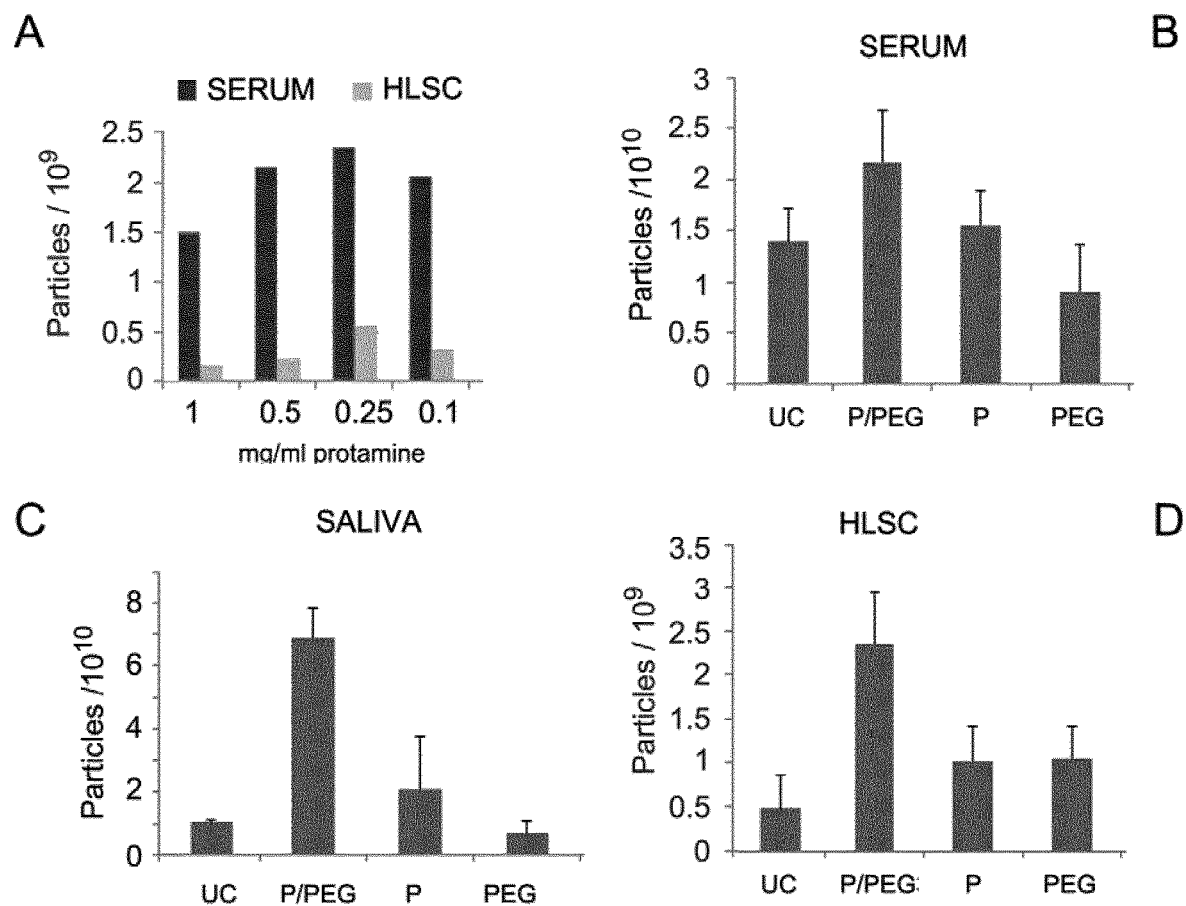
FIGS. 1A-C graphically depict the results of experiments comparing the number of particles (EVs) precipitated and recovered from different media using different precipitation agents.

The method of isolating extracellular vesicles (EVs) according to the present invention results from the finding that EVs display a negative charge, which allows them to interact with positive-charged molecules.

Based on this finding, the inventors precipitated EVs from biological fluids and cell culture conditioned media in the presence of positively-charged protamine in a polymeric matrix, and compared the efficiency with that of ultracentrifugation, in terms of yield of number of recovered vesicles, efficiency of RNA extraction, exosomal protein expression and biological activity.

Protamine was surprisingly found to induce EV precipitation without the need of ultracentrifugation. Moreover, EV resuspension was facilitated when protamine (P) precipitation was performed in the presence of an extracellular matrix forming polymer. The recovery of precipitated EVs evaluated by NanoSight analysis was more efficient than that obtained by ultracentrifugation. By electron microscopy, the size of EVs was similar with the two methods, and the expression of CD63, CD9 and CD 81 exosomal markers in the EVs isolated according to the method of the present invention indicated an enrichment in exosomes. The RNA recovery of the EVs isolated according to the method of the present invention was similar to that of EV isolated by ultracentrifugation. Moreover, the EVs isolated according to the method of the present invention retained the biological activity in vitro as seen by the induction of wound closure by keratinocytes and of proliferation of tubular epithelial cells. In summary, the isolation of EVs according to the method of the present invention has the merit of simplicity and avoids requirement of expensive equipment and may be used for an efficient isolation of EVs from small biological samples.

The method of isolating extracellular vesicles (EVs) from a biological fluid sample according to the present invention comprises the steps of mixing the biological fluid sample with a polycationic substance and an extracellular matrix forming polymer, incubating the resulting mixture, thereby achieving precipitation of EVs, and separating the precipitated EVs from the mixture.

A polycationic substance is a polymeric molecule having positive charges in multiple places. Any polycationic substance may be used in the method of the invention, on account of the fact that EVs are negatively charged and polycations are able to aggregate them.

Preferred polycationic substances have a molecular weight of 0.5-50 kDa and/or a positive zeta potential of 2-20 mV.

Protamine, preferably in the form of a salt, is more preferred because it is suitable for clinical applications. The most preferred form of protamine is protamine chloride or hydrochloride. Suitable alternatives to protamine are for example polylysine or cationic dextrans such as DEAE dextran, preferably in the form of a salt such as hydrochloride.

The polycationic substance, preferably the salt of protamine, is preferably mixed with the extracellular matrix forming polymer and the biological fluid sample to result in a concentration of 0.02-2 mg/ml in the mixture.

The extracellular matrix forming polymer suitable for use in the method of the invention is any polymeric substance which is capable of forming a mesh-like net which embed the EVs contained in the biological fluid sample. Preferably, the extracellular matrix forming polymer is a hydrogel. Hydrogel-forming natural polymers include proteins such as collagen and gelatine and polysaccharides such as starch, alginate, and agarose. Synthetic polymers that form hydrogels are traditionally prepared using chemical polymerization methods. More preferably the extracellular matrix forming polymer is selected from the group consisting of polyethylene glycol, dextran, dextran sulfate, dextran acetate, polyvinyl alcohol, polyvinyl acetate, or polyvinyl sulfate, polyvinylpyrrolidon, hyaluronic acid, hydroxy ethyl starch. Polyethylene glycol (PEG) having an average molecular weight comprised within the range of from 4 to 100 kDa is the preferred extracellular matrix forming polymer. More preferably, PEG having an average molecular weight comprised within the range of from 10 to 50 kDa, even more preferably of about 35 kDa, is employed in the method of the invention.

Examples of preferred polycationic substance/extracellular matrix forming polymer pairs for use in the method of the present invention are:
  (i) Protamine (P)+PEG,
  (ii) poly-L-lysine+PEG,
  (iii) poly-L-lysine+dextran sulfate,
  (iv) DEAE dextran+PEG.

All of these polycationic substance/extracellular matrix forming polymer pairs were experimentally tested and proved to be effective in precipitating EVs from serum samples (see the examples).

According to a preferred embodiment of the method of the invention, the extracellular matrix forming polymer is mixed with the polycationic substance and with the biological fluid sample to result in a concentration of 0.01-0.2 g/ml in the mixture.

In order to separate the precipitated EVs from the mixture, any separation technique which may prevent the risk of disrupting the integrity of the EV membranes may be used. A preferred method is centrifugation, at a speed preferably comprised within the range of from 1000 to 50000 g, more preferably of from 1000 to 10000 g, even more preferably of from 1000 to 5000 g.

As it will be illustrated in more detail in the following experimental examples, the inventors employed the method of the invention to isolate EVs from both biological fluids (serum and saliva) and from cell culture conditioned media (HLSCs). Accordingly, the method of the invention can be used for isolating EVs from any biological fluid or cell culture conditioned medium, such as for example from blood, serum, plasma, saliva, urine, cerebrospinal fluid, or from a cell culture conditioned medium, preferably an adult stem cell culture conditioned medium, more preferably a mesenchymal stem cell culture conditioned medium or a liver pluripotent progenitor cell culture conditioned medium.

The scope of the invention also comprises a composition for precipitation of extracellular vesicles (EVs) from a biological fluid sample, which is suitable for use in the method according to the invention. Such a composition comprises a vehicle (preferably water, e.g. distilled water), as well as the polycationic substance and the extracellular matrix forming polymer as previously defined in relation to the method. Since the inventors found that the preferred volume ratio of the precipitation solution to the biological fluid is of about 4, of the precipitation composition of the present invention preferably includes the extracellular matrix forming polymer at a concentration comprised within the range of from 0.05 to 1 g/ml and the polycationic substance at a concentration comprised within the range of from 0.1 to 10 mg/ml.

The following examples are provided by way of illustration only and are not intended to limit the scope of the invention as determined by the appended claims.

The examples were carried out by using protamine as the polycationic substance and PEG 35000 Da as the extracellular matrix forming polymer. The inventors compared this technique, which in the following shall be designated as "P/PEG precipitation" or more briefly as "P/PEG", with the differential ultracentrifugation which is the gold standard for EV isolation.

The following examples show that P/PEG was more efficient for the recovery of EVs from small volumes of serum and saliva as well as from the conditioned medium of cultured cells than ultracentrifugation, as judged by NTA.

The size of EVs, as observed by electron microscopy, was similar but the membrane debris present in the ultra-centrifuged EVs were absent in P/PEG EV preparations. In particular, EVs precipitated from saliva were very homogeneous in size and shape.

The expression of exosomal markers in EVs obtained by P/PEG precipitation suggests an enrichment in exosomes in these precipitates.

Since one of the main concerns for EVs obtained by precipitation methods is the presence of contaminants of non-vesicular origin, such as lipoproteins, the inventors also evaluated the presence of Apo B100 and Apo A in the different preparations obtained. The results indicate that in serum EVs, Apo B100 and Apo A1 were present not only in EV precipitates but also in EVs purified by differential ultracentrifugation. This may be a limitation for the use of serum EVs for diagnostic proposes if the intent is to discriminate exRNA associated with vesicles from those associated with lipoproteins. However, detection of exRNA in the biological sample may be exploited for liquid biopsy independently from their vehicle and precipitation techniques may be suitable for this purpose. Apo B100 and Apo A1 were absent or barely detectable in saliva EVs and in EVs purified from culture media by P/PEG preparations, suggesting that lipoprotein contamination is less relevant for these biological samples.

The use of Sephadex G-25 spin columns has been suggested to remove PEG 8000 containing lipoproteins from precipitated EVs (1). Since the inventors precipitated EVs with protamine in association with PEG 35000 Da, Sephadex G 100 spin columns were used showing the effective removal of apo-lipoprotein contaminants. After absorption, the total RNA was reduced but still suitable for detection of miRNA and mRNA content of EVs.

EVs obtained by P/PEG precipitation retained the biological activity in vitro, as shown by the induction of wound closure by keratinocytes stimulated with EVs from saliva and by induction of proliferation of tubular epithelial cells challenged with EVs released by HLSC.

Further experiments were carried out with different polycationic substance/extracellular matrix forming polymer pairs, which proved to be effective in favouring EVs precipitation.

All prior art methods available for EV purification have some advantages and disadvantages and possibly no one is ideal for every application. The herein described method has the merit of simplicity and avoids requirement of expensive equipment. In addition, the isolated EVs retained the biological activities.

In conclusion, the inventors showed that the precipitation method of the present invention provides for efficient isolation of EVs from biological samples and may be exploited for search of new biomarkers.

EXAMPLES

Materials and Methods
Biological Samples
Saliva was obtained from adult normal volunteers (n=5). Human serum from healthy donors (n=5) was provided by the Blood Bank of Città della Salute e della Scienza di Torino, after informed consent and approval by the internal Review Board of Blood Bank.

Adult human Liver Stem Cells (HLSCs).
HLSCs were isolated from human cryopreserved normal adult hepatocytes (Lonza, Basel, Switzerland) cultured and characterized as previously described (2). Concisely, hepatocytes first cultivated for 2 weeks in Hepatozyme-SFM medium then in α-MEM/EBM-1 (3:1) (Invitrogen, Carlsbad, Calif.) media added with Hepes (12 mM, pH 7.4), 1-glutamine (5 mM) penicillin (50 IU/ml), streptomycin (50 µg/ml) (all from Sigma, St. Louis, Mo., USA), and fetal calf serum (FCS) (10%) (Invitrogen), Cells were expanded and characterized. The characterization of HLSCs by cytofluorimetric analysis demonstrated the expression of the mesenchymal stem cell markers but not the endothelial and hematopoietic markers as described (3). HLSCs also expressed alpha-fetoprotein and human albumin and the vimentin and nestin resident stem cell markers, but not CD34, CD117 and cytocheratin 19 oval cell markers (2). In addition, HLSCs were positive for the nanog, Sox2, Oct4, and SSEA4 embryonic stem cell markers (4). HLSCs under proper culture conditions underwent endothelial, osteogenic and hepatic differentiation (2).

Keratinocytes
Keratinocytes (HaCaT) were purchased from Lonza (Lonza, Basel, Switzerland) and cultured with KBM-gold basal medium (Lonza, Basel, Switzerland) at 37° C. with 5% $CO_2$. Cells were seeded at density 3500 cell/cm$^2$, using 1 ml of medium per cm$^2$ and subcultured when cell confluence was 70-80%. Briefly, flasks were washed with HEPES buffer saline solution, incubated with trypsin solution for 6 minutes and then trypsin was neutralized with medium containing 10% FCS. If cells were not completely detached within 7 minutes, incubation with trypsin was repeated.

Renal Tubular Epithelial Cells (TEC)
TEC line immortalized by infection with a hybrid Adeno5/SV40 virus was previously developed by Cantaluppi et al. (5). Cells were grown with DMEM (Lonza, Basel, Switzerland) containing 10% FCS (GIBCO) and 2 mM glutamine (Life Technologies).

TEC showed negative staining for von Willebrand factor, minimal staining for desmin and vimentin, and marked staining with antibodies directed to cytokeratins and actin. TEC were also positive for markers of fully differentiated proximal TEC such as alkaline phosphatase, aminopeptidase A, and megalin.

Isolation of EVs

EVs were purified from HLSC culture media, human serum and saliva. EVs isolated from supernatants of HLSCs ($2.10^6$ cells/T75) were obtained after 24 hour culture in RPMI deprived of FCS. At the time of EV isolation, the 97-99% of cells was viable by trypan blue exclusion assay and TUNEL assay did not detect apoptotic cells.

Saliva samples (5 ml) were collected in sterile tubes and kept in ice during harvest. One hour before donation, healthy donors followed a protocol of fasting without drinking and eating.

Serum samples were collected from healthy donors using serum separating tubes (BD) centrifuged 1500 g for 15 minutes.

Before isolation procedures, HLSC supernatant, saliva and serum samples were submitted to two centrifugations at 3000 g for 20 minutes in order to remove cell debris and other contaminants. The saliva samples were diluted 1:1 with PBS and filtered with 0.22 µm filters.

Differential Ultracentrifugation

After removal of cell debris and apoptotic bodies by two centrifugations at 3,000 g for 20 minutes, EVs were purified as described by Thery et al (10) by a first ultracentrifugation at 10,000 g followed by ultracentrifugation at 100,000 g for 1 hour at 4° C. (Beckman Coulter Optima L-90K, Fullerton, Calif., USA).

Charge-Based Precipitation

The biological samples ready for precipitation procedure were transferred in sterile vials and added with the protamine (P) (Sigma, St. Louis, Mo., USA)/Polyethylene glycol (PEG 35000 Merck KGaA, Darmstadt, Germany) precipitation solution (P/PEG) (1 volume precipitation solution: 4 volume sample). As a control, P or PEG 35000 alone (PEG) were used. The composition of precipitation solution was 0.25 g Polyethylene glycol (PEG 35000, Merck) and 1 mg protamine hydrochloride/ml (Sigma) of distilled water.

After overnight incubation at 4° C., the mixture was centrifuged at 1500 g for 30 minutes at room temperature and the supernatant discarded. The pellet was re-suspended in the appropriate buffer to study biological activities or in lysis buffer for RNA extraction and Western Blot analysis.

To remove lipoproteins Sephadex G-100 (GE Healthcare Bio-Sciences AB, Uppsala, Sweden) spin columns were used. EVs were recovered in the void volumes.

Measure of EV Charge

The analysis was performed by Zeta-sizer nanoinstrument (Malvern Instruments SA, Vénissieux, France; Size range: 0.3 nm-10 µm). Zeta-potential (slipping plane) is generated at x distance from the particle indicating the degree of electrostatic repulsion between adjacent, similarly charged particles in a dispersion. Negative Zeta-potential indicates a high grade of dispersion across the particles.

Nanoparticle Tracking Analysis (NTA)

NanoSight LM10 (Malvern Instruments SA) was used to analyze concentration and size distribution of EVs by means of the NTAsoftware. The Brownian movements of EVs present in the sample subjected to a laser light source were recorded by a camera and converted into size and concentration parameters by NTA through the Stokes-Einstein equation.

Transmission Electron Microscopy

Transmission electron microscopy was performed on EVs isolated by ultracentrifugation or charge-based precipitation resuspended in PBS, placed on 200 mesh nickel formvar carbon coated grids (Electron Microscopy Science, Hatfield, Pa.) and left to adhere for 20 min. Grids were then incubated with 2.5% glutaraldehyde containing 2% sucrose and after washings in distilled water the EVs were negatively stained with NanoVan (Nanoprobes, Yaphank, N.Y., USA) and observed by Jeol JEM 1010 electron microscope (Jeol, Tokyo, Japan).

Western Blot Analysis

Protein content of the EV preparations was quantified by Bradford method (Bio-Rad, Hercules, Calif., USA). Protein samples were separated by 4% to 15% gradient sodium dodecyl sulfate-polyacrylamide gel electrophoresis and subjected to immunoblotting with rabbit polyclonal antibodies anti-CD9, CD63, CD81, anti-apoliporotein B100 and goat polyclonal antibody anti-apolipoprotein A1 (Abcam, Cambridge UK). The protein bands were visualized with an enhanced chemiluminescence (ECL) detection kit and ChemiDoc™ XRS+System (BioRad). Cell and EV lysates were loaded at concentration of 30 µg/well.

RNA Extraction

The mirVana RNA isolation kit (Thermo Fisher Scientific, Waltham, Mass., USA) has been used to extract total RNA from EVs following the manifacturer's procedure and the RNA has been spectrophotometrically quantified (Nanodrop ND-1000, Wilmington, Del., USA).

miRNA and mRNA Profiling by Quantitative Real-Time PCR

Quantitative real-time PCR was carried out as previously described (6) using a 48-well StepOne™ Real Time System (Applied Biosystems, Waltham, Mass., USA). Concisely, 0.2 µg RNA were first reverse transcribed using miScript Reverse Transcription Kit, then 3 ng of cDNA in triplicate were employed to identify and measure significant miRNAs performing qRT-PCR with miScript SYBR Green PCR kit (Qiagen, Valencia, Calif.) USA). miRNA specific primers to hsa-miR-16, 29a, 99b, 191, 223 were used in separate reactions. The RNU44 and RNU48 snoRNAs served as positive controls and 10 µl of water were used as negative controls in place of the RNA.

qRT-PCR analysis was also performed on Saliva EVs for the presence of IL8 and Meosin, mRNA and on HLSC EVs for the presence of Ago2 and GAPDH mRNA.

Cell Proliferation Assays

Immortalized tubular epithelial cells (TEC) were seeded at a density of $3 \times 10^3$ cells/well in 96 well plates in DMEM supplemented with 10% FCS. 12 hours later, TEC were starved with medium w/o FCS for 2 hours, stimulated with HLSC EVs and then 10 µM BrdU was added overnight. The plates were analyzed by BrdU kit (BrdU; Roche Diagnostics) and the absorption values were determined at 405 nm wavelength.

In vitro Scratch-Wound Healing Assay

HACAT cells were seeded at a density of about $50 \times 10^3$ cells/well in a 24 well plates in DMEM supplemented with 10% FCS. When cells reached the complete confluence, they were starved with medium w/o FCS overnight. The day after, scratch wounds were created with a sterile tip. Before stimulation (t=0), micrographs of the well were acquired with LEICA microscope. Cells were then stimulated with EVs (50,000 EVs per target cells) isolated from saliva of three different donors. The 'wound closure' phenomenon was monitored for 36 h using the LEICA microscope and images were analyzed by image J software observing the decrease of wound area in cells stimulated with saliva EVs in comparison to cells not stimulated with EVs.

Statistical Analysis

Results are expressed as mean±SD. Statistical analysis was performed by using ANOVA with Dunnet's multicomparison tests when appropriate. P<0.05 was considered significant.

Results

The analysis of Zeta potential was performed on different biological samples showing that EVs display a negative charge (Table 1).

TABLE 1

| Zeta potential | mV |
|---|---|
| HLSC EVs | −13,800 mV |
| Serum EVs | −7,825 mV |
| Saliva EVs | −8.54 mV |

In preliminary experiments serum was incubated with different doses of protamine (1, 0.5, 0.25, 0.1 mg/ml) overnight at 4° C. and precipitated EVs were recovered by centrifugation at 3000 g for 30 minutes (FIG. 1A). However, the EV pellet was easily re-suspended with the dose of 0.25 mg protamine/ml serum whereas highest dose generated pellets more difficult to re-suspend. We observed that addition of PEG 35,000 to protamine favored resuspension. On this basis, a precipitation strategy was set to favor precipitation of negative charged EVs into a polymeric matrix that would allow the recovery of EVs after centrifugation without the need of an ultracentrifugation step.

FIG. 1 shows the comparison by NTA of EV recovery from serum (B), saliva (C) and cell free supernatant of HLSC (D) after ultracentrifugation (UC) or precipitation with P/PEG, PEG alone and protamine alone. The results indicate that P/PEG precipitation was more efficient than other conditions in terms of number of EVs detected by NTA. The size of EVs isolated in the different conditions was similar as seen by transmission electron microscopy. Serum derived EVs ranged from 35 to 95 nm, whereas those derived from saliva were a more homogeneous population with a size ranging from 45 to 65 nm. EVs derived from HLSC ranged from 45 to 75 nm (FIG. 2A).

Figure 2:
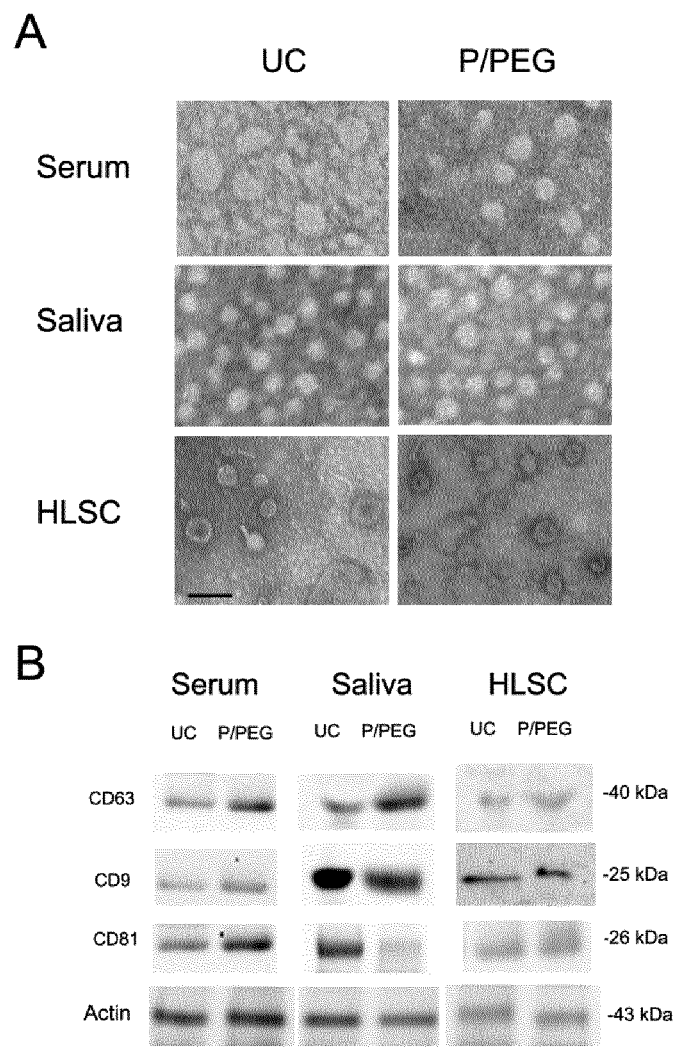
FIG. 2A contains transmission electron microscopy images of EVs isolated from different media under different conditions.
FIG. 2B contains Western blot analysis images of EVs precipitated from different media using different precipitating agents.
Figure 3:
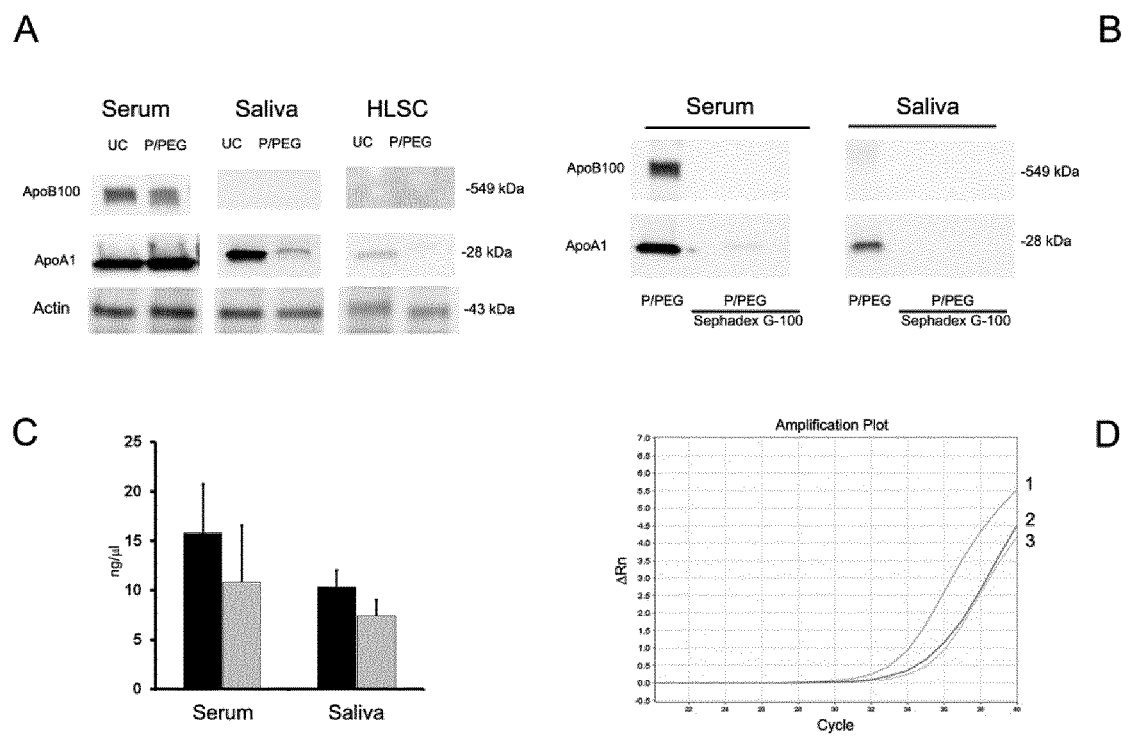
FIG. 3A contains Western blot analysis images of EVs obtained by ultracentrifugation from different media using different precipitation agents.
FIG. 3B contains gel-filtration images of EVs recovered from different media using different precipitation agents.
FIG. 3C graphically depicts the amount of RNA extracted from EVs isolated from different media both before and after Sephadex G-100 pre-absorption.
FIG. 3D graphically depicts the results of a PCR analysis of mRNA present in serum EVs.

As for EVs obtained by ultracentrifugation, the Western blot analysis of EVs precipitated from serum, saliva and HLSC by P/PEG showed the expression of CD63, CD9 and CD 81 exosomal markers (FIG. 2B). Since it has been suggested that precipitation techniques co-isolate contaminant lipoproteins (7, 8), we evaluated by Western blot the presence of Apo B100 and Apo A1 in EVs obtained by ultracentrifugation and P/PEG precipitation. As shown in FIG. 3A, Apo B100 and Apo A1 were detected in serum EVs obtained both by ultracentrifugation and precipitation. In saliva EVs Apo B100 was absent. Apo A1 was detectable in EVs obtained from saliva after ultracentrifugation whereas was barely detectable in P/PEG precipitation samples. Apo B100 was absent in EVs purified from HLSC culture media both by ultracentrifugation and precipitation, whereas Apo A1 was detectable only in EVs purified by ultracentrifugation. To remove lipoproteins, Sephadex G-100 spin columns were used and the EVs were recovered in the void volumes whereas apo-lipoproteins were retained. As seen in FIG. 3B, gel-filtration with Sephadex G-100 removed Apo B100 and Apo A1 from EV preparations.

Detection of RNAs in EVs

Figure 4:
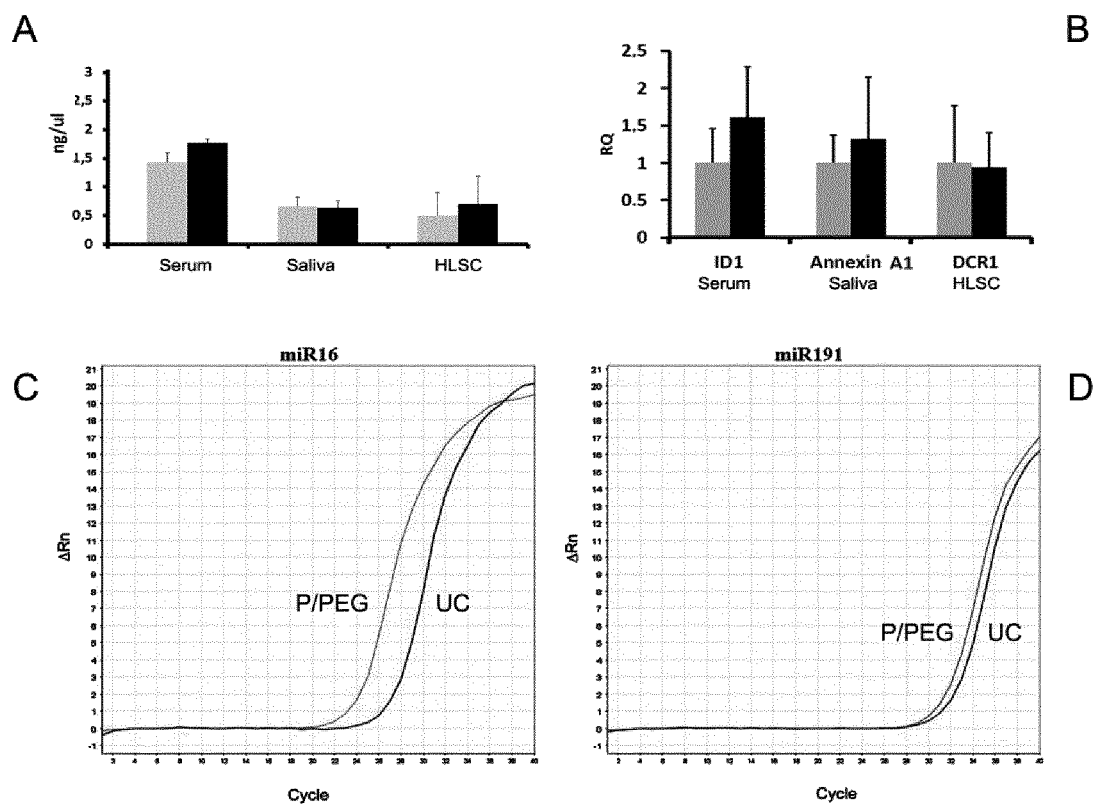
FIG. 4A graphically depicts a comparison between RNA extracted from EVs prepared by precipitation and by ultracentrifugation.
FIG. 4B graphically depicts the results of a qRT-PCR analysis for the detection of mRNA in EVs derived from different media and purified by ultracentrifugation compared with that purified by precipitation.
FIG. 4C graphically depicts the results of a RT-PCR analysis comparing the amounts of miR16 in EVs isolated using precipitation and ultracentrifugation.
FIG. 4D, like FIG. 4C, graphically depicts a representative amplification plot but for the relative amounts of miR191 in EVs obtained by ultracentrifugation and precipitation.

As shown in FIG. 3C, the amount of RNA extracted after Sephadex G-100 pre-absorption was reduced both in serum and in saliva but the difference was not statistically significant. PCR analysis showed also a reduction of about 2 cycles of a representative mRNA present in serum EVs (ID1 mRNA; FIG. 3D). FIG. 4 shows a comparison between RNA extracted from EVs prepared by P/PEG precipitation and by ultracentrifugation. No significant difference of RNA content was observed between EVs isolated by the two methods. To evaluate whether RNA extracted from EVs prepared by P/PEG precipitation was suitable for detection of miRNAs or mRNA, RT-PCR analysis was performed. RT-PCR analysis showed the presence of comparable amount of miR16, 29a, 99b, 191 e 223, in EVs isolated from normal subjects using both techniques (FIG. 4C). In contrast, miR500, 142-3p, 127-3p, and 155 were either undetectable or detectable in very low level (not shown). FIG. 4D shows a representative amplification plot for miR191 in EVs obtained by ultracentrifugation and precipitation. We also performed qRT-PCR analysis for detection of mRNA. As shown in FIG. 4B, comparable amounts of selected mRNA were detected in EVs derived from serum, saliva and HLSC either purified by ultracentrifugation or P/PEG precipitation.

Evaluation of Capability of EVs Isolated by Charge-Bbased Precipitation to Retain Bbiological Activities The biological activity of EVs obtained by ultracentrifugation and by P/PEG precipitation was evaluated for saliva and HLSC EVs.

Figure 5:
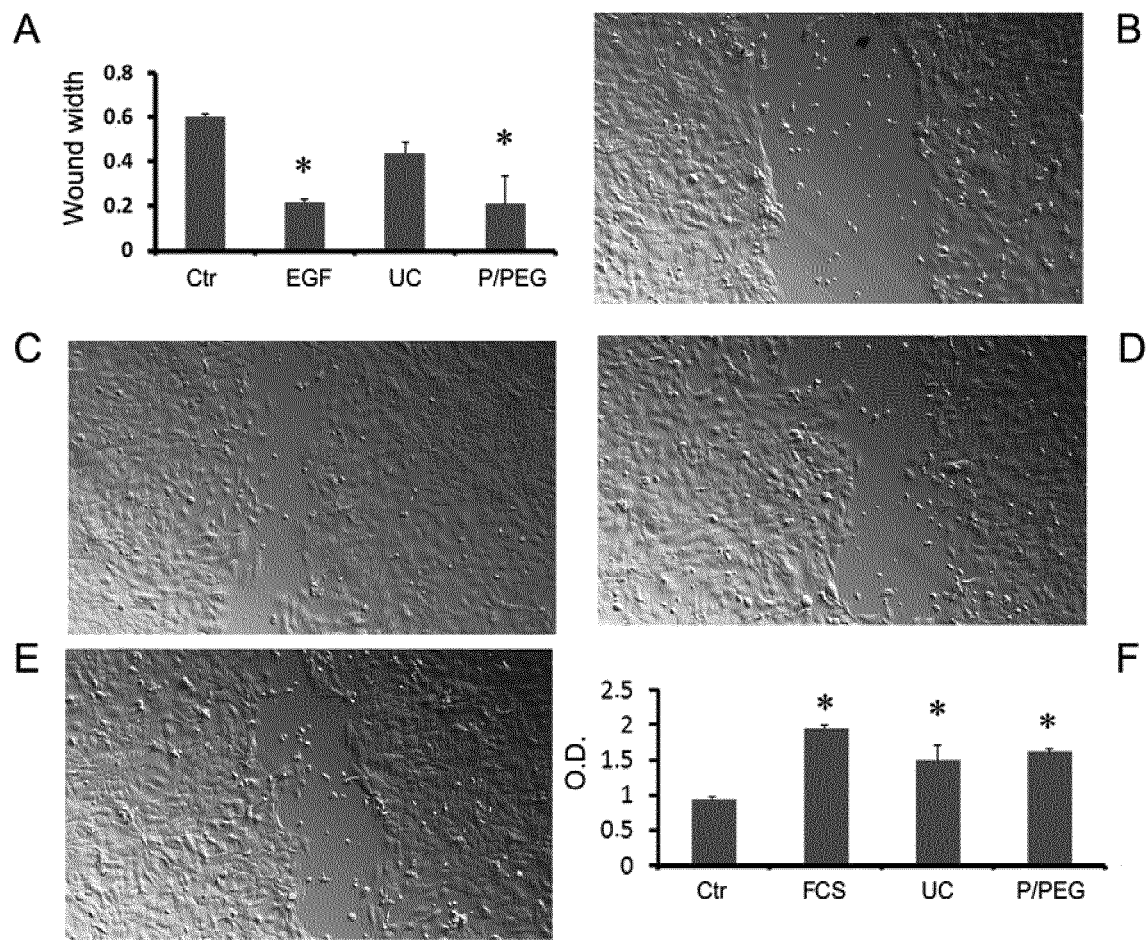

In order to test the biological activity of saliva EVs we performed in vitro wound-closure assay using human HaCaT keratinocytes. Saliva EVs obtained by P/PEG induced a significant wound closure comparable to that of EGF (FIG. 5A-E). In particular, precipitated EVs were more effective than EVs obtained by ultracentrifugation (FIG. 5E).

In order to test the biological activity of HLSC EVs we performed in vitro proliferation of tubular epithelial cells. Both precipitated and ultra-centrifuged EVs were able to significantly increase cell proliferation (FIG. 5F).

Additional Polycationic Substance/Extracellular Matrix Forming Polymer Pairs Tested

| Tested substances | Mean intensity of PKH26-labeled serum EVs |
|---|---|
| Protamine chloride + PEG | 79 ± 11 |
| Poly-L-lysine | 57 ± 18 |
| Poly-L-lysine + Dextran sulfate | 74 ± 42 |
| PEG | 50 ± 12 |
| Poly-L-lysine + PEG | 73 ± 39 |
| DEAE Dextran | 49 ± 14 |
| PEG + DEAE Dextran | 79 ± 11 |

The table shows the fluorimetric determination of serum extracellular vesicles (EVs) labeled with the fluorescent red dye PKH26, precipitated with the indicated substances and resuspended in phosphate buffered saline (PBS). Quantitation is expressed as the mean intensity of fluorescence. The effective labeling was verified by confocal microscopy.

The results obtained show that: a) all of the tested polycationic substances are effective in favoring precipitation of EVs from serum samples, and b) a precipitation solution comprising a polymeric substance/extracellular matrix forming polymer pair is more effective than a precipitation solution comprising either the polymeric substance alone or the extracellular matrix forming polymer alone.

REFERENCES

1. Szatanek R, Baran J, Siedlar M and Baj-Krzyworzeka M: Isolation of extracellular vesicles: Determining the correct approach (Review). Int J Mol Med 36: 11-17, 2015.

2. Herrera M B, Bruno S, Buttiglieri S, Tetta C, Gatti S, Deregibus M C, Bussolati B and Camussi G. Isolation and characterization of a stem cell population from adult human liver. Stem Cells 24: 2840-2850, 2006.

3. Ratajczak J, Wysoczynski M, Hayek F, Janowska-Wieczorek A and Ratajczak M Z: Membrane-derived microvesicles: important and underappreciated mediators of cell-to-cell communication. Leukemia 20: 1487-1495, 2006.

4. Herrera M B, Fonsato V, Gatti S, Deregibus M C, Sordi A, Cantarella D, Calogero R, Bussolati B, Tetta C and Camussi G: Human liver stem cell-derived microvesicles accelerate hepatic regeneration in hepatectomized rats. J Cell Mol Med 14: 1605-1618, 2010.

5. Cantaluppi V, Biancone L, Romanazzi G M, Figliolini F, Beltramo S, Galimi F, Camboni M G, Deriu E, Conaldi P, Bottelli A, Orlandi V, Herrera M B, Pacitti A, Segoloni G P and Camussi G: Macrophage stimulating protein may promote tubular regeneration after acute injury. J Am Soc Nephrol 19: 1904-1918, 2008.

6. Iavello A, Frech V S, Gai C, Deregibus M C, Quesenberry P J and Camussi G: Role of Alix in miRNA packaging during extracellular vesicle biogenesis. Int J Mol Med 37: 958-966, 2016

7. Witwer K W, Buzás E I, Bemis L T, Bora A, Lässer C, Lötvall J, Nolte-'t Hoen E N, Piper M G, Sivaraman S, Skog J, Théry C, Wauben M H and Hochberg F: Standardization of sample collection, isolation and analysis methods in extracellular vesicle research. J Extracell Vesicles 2: 20360, 2013.

8. Momen-Heravi F, Balaj L, Alian S, Trachtenberg A J, Hochberg F H, Skog J and Kuo W P: Impact of biofluid viscosity on size and sedimentation efficiency of the isolated microvesicles. Front Physiol 3: 162, 2012.

The invention claimed is:

1. A method of isolating extracellular vesicles (EVs) from a biological fluid sample, the method comprising the steps of:
   (i) mixing the biological fluid sample with a polycationic substance and an extracellular matrix forming polymer;
   (ii) incubating the mixture, thereby achieving precipitation of the EVs; and
   (ii) separating the precipitated EVs from the mixture.

2. The method according to claim 1, wherein the step of separating the precipitated EVs from the mixture is effected by centrifugation.

3. The method according to claim 1, wherein the polycationic substance is a protamine salt, a polylysine salt, or a cationic dextran salt.

4. The method according to claim 3, wherein the salt is a hydrochloride.

5. The method according to claim 1, wherein the extracellular matrix forming polymer is a hydrogel.

6. The method according to claim 1, wherein the extracellular matrix forming polymer is selected from the group consisting of collagen, gelatine, starch, alginate, agarose, polyethylene glycol, dextran, dextran sulfate, dextran acetate, polyvinyl alcohol, polyvinyl acetate, polyvinyl sulfate, polyvinylpyrrolidone, hyaluronic acid, and hydroxy ethyl starch.

7. The method according to claim 1, wherein biological fluid is selected from the group consisting of blood, serum, plasma, saliva, urine, cerebrospinal fluid, and the conditioned medium of a cell culture.

8. The method according to claim 7, wherein the cell culture is an adult stem cell culture.

9. The method according to claim 1, wherein the polycationic substance is mixed with the extracellular matrix forming polymer and with the biological fluid sample to result in a concentration of 0.02-2 mg/ml in the mixture.

10. The method according to claim 1, wherein the extracellular matrix forming polymer is mixed with the polycationic substance and with the biological fluid sample to result in a concentration of 0.01-0.2 g/ml in the mixture.

11. The method according to claim 1, wherein the extracellular matrix forming polymer has an average molecular weight within the range of from 4 to 100 kDa.

12. The method according to claim 2, wherein centrifugation is carried out at 1000-50000 g.

13. The method according to claim 2, wherein centrifugation is carried out at 100-10000 g.

14. The method according to claim 2, wherein centrifugation is carried out at 1000-5000 g.

15. The method according to claim 7, wherein the cell culture is an adult mesenchymal stem cell culture or an adult liver pluripotent progenitor cell culture.

* * * * *